(12) United States Patent
Tipsmark et al.

(10) Patent No.: US 8,012,126 B2
(45) Date of Patent: Sep. 6, 2011

(54) INFUSION SET

(75) Inventors: Henrik Tipsmark, Roskilde (DK); Jens Egebjerg Nielsen, Ringsted (DK)

(73) Assignee: Unomedical A/S, Birkeroed (DK)

( * ) Notice: Subject to any disclaimer, the term of this patent is extended or adjusted under 35 U.S.C. 154(b) by 0 days.

(21) Appl. No.: 12/446,859

(22) PCT Filed: Oct. 29, 2007

(86) PCT No.: PCT/DK2007/000459
§ 371 (c)(1),
(2), (4) Date: Sep. 14, 2009

(87) PCT Pub. No.: WO2008/052545
PCT Pub. Date: May 8, 2008

(65) Prior Publication Data
US 2010/0022956 A1    Jan. 28, 2010

Related U.S. Application Data

(60) Provisional application No. 60/855,554, filed on Oct. 31, 2006.

(30) Foreign Application Priority Data

Oct. 31, 2006  (EP) .................................. 06022674

(51) Int. Cl.
*A61M 37/00*  (2006.01)
(52) U.S. Cl. ...................................... 604/154
(58) Field of Classification Search ............. 604/164.01, 604/164.07, 257, 533, 539
See application file for complete search history.

(56) References Cited

U.S. PATENT DOCUMENTS 1,592,462 A    7/1926 MacGregor
(Continued)

FOREIGN PATENT DOCUMENTS

DE    4 342 329 A1    6/1994
(Continued)

OTHER PUBLICATIONS

International Search Report completed Jan. 11, 2008 for International Application No. PCT/DK2007/000459.
(Continued)

*Primary Examiner* — Nicholas D Lucchesi
*Assistant Examiner* — Aarti B Berdichevsky
(74) *Attorney, Agent, or Firm* — Brinks Hofer Gilson & Lione (57) ABSTRACT

The application relates to an infusion set comprising an infusion part (1) comprising a base part (3) having a main plane, a head part (6) extending from the main plane of the base part and a cannula (12) extending from the base part, first fastening means, a connector (2) having a plane being parallel to and above the main piano of the base part, and having one or more arms (15), said arms being fastened to the connector at a first end, and being free in a second opposite end, and a tube (14), guide means (7, 16) second fastening means (8, 17) being in the form of projecting connector retention devices (17) positioned on the arms of the connector adapted to engage with retention devices (8) extending from the base part, where the plane of the connector can be tilted to a distance from the base part causing the second to be displaced to a distance from that is larger than the height (h) of the retention devices.

20 Claims, 5 Drawing Sheets

U.S. PATENT DOCUMENTS

| | | |
|---|---|---|
| 2,047,010 A | 7/1936 | Dickinson |
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,610,240 A | 10/1971 | Harautuneian |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,525,157 A | 6/1985 | Vaillancourt |
| 4,530,695 A | 7/1985 | Phillips et al. |
| 4,531,937 A | 7/1985 | Yates |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |

| | | | | | |
|---|---|---|---|---|---|
| 5,599,315 A | 2/1997 | McPhee | 6,139,534 A | 10/2000 | Niedospial, Jr. |
| 5,599,318 A | 2/1997 | Sweeney et al. | 6,159,181 A | 12/2000 | Crossman et al. |
| 5,628,765 A | 5/1997 | Morita | 6,183,464 B1 | 2/2001 | Sharp et al. |
| 5,643,214 A | 7/1997 | Marshall | 6,191,338 B1 | 2/2001 | Haller |
| 5,643,216 A | 7/1997 | White | 6,193,694 B1 | 2/2001 | Bell et al. |
| 5,643,220 A | 7/1997 | Cosme | 6,210,420 B1 | 4/2001 | Mauze et al. |
| 5,662,617 A | 9/1997 | Odell et al. | 6,219,574 B1 | 4/2001 | Cormier et al. |
| 5,665,071 A | 9/1997 | Wyrick | 6,221,058 B1 | 4/2001 | Kao et al. |
| 5,665,075 A | 9/1997 | Gyure et al. | 6,248,093 B1 | 6/2001 | Moberg |
| 5,676,156 A | 10/1997 | Yoon | 6,293,925 B1 | 9/2001 | Safabash et al. |
| 5,681,323 A | 10/1997 | Arick | 6,302,866 B1 | 10/2001 | Marggi |
| 5,695,476 A | 12/1997 | Harris | 6,319,232 B1 | 11/2001 | Kashmer |
| 5,697,907 A | 12/1997 | Gaba | 6,322,535 B1 | 11/2001 | Hitchins et al. |
| 5,700,250 A | 12/1997 | Erskine | 6,322,808 B1 | 11/2001 | Trautman et al. |
| 5,702,371 A | 12/1997 | Bierman | 6,334,856 B1 | 1/2002 | Allen et al. |
| 5,704,920 A | 1/1998 | Gyure | 6,355,021 B1 | 3/2002 | Nielsen et al. |
| 5,714,225 A | 2/1998 | Hansen et al. | 6,379,335 B1 | 4/2002 | Rigon et al. |
| 5,738,641 A | 4/1998 | Watson et al. | 6,387,076 B1 | 5/2002 | Landuyt |
| 5,741,288 A | 4/1998 | Rife | 6,387,078 B1 | 5/2002 | Gillespie, III |
| 5,752,923 A | 5/1998 | Terwilliger | 6,405,876 B1 | 6/2002 | Seshimoto et al. |
| 5,807,316 A | 9/1998 | Teeple | 6,440,096 B1 | 8/2002 | Lastovich et al. |
| 5,807,348 A | 9/1998 | Zinger et al. | 6,447,482 B1 | 9/2002 | Rønborg et al. |
| 5,810,835 A | 9/1998 | Ryan et al. | 6,450,992 B1 | 9/2002 | Cassidy, Jr. |
| 5,817,058 A | 10/1998 | Shaw | 6,488,663 B1 | 12/2002 | Steg |
| 5,820,598 A | 10/1998 | Gazza et al. | 6,503,222 B1 | 1/2003 | Lo |
| 5,827,236 A | 10/1998 | Takahashi | 6,517,517 B1 | 2/2003 | Farrugia et al. |
| 5,833,666 A | 11/1998 | Davis et al. | 6,520,938 B1 | 2/2003 | Funderburk et al. |
| 5,843,001 A | 12/1998 | Goldenberg | D472,316 S | 3/2003 | Douglas et al. |
| 5,848,990 A | 12/1998 | Cirelli et al. | D472,630 S | 4/2003 | Douglas et al. |
| 5,851,197 A | 12/1998 | Marano et al. | 6,572,586 B1 | 6/2003 | Wojcik |
| 5,858,001 A | 1/1999 | Tsals et al. | 6,579,267 B2 | 6/2003 | Lynch et al. |
| 5,865,806 A | 2/1999 | Howell | 6,582,397 B2 | 6/2003 | Alesi et al. |
| 5,899,886 A | 5/1999 | Cosme | 6,595,962 B1 | 7/2003 | Perthu |
| 5,911,705 A | 6/1999 | Howell | 6,607,509 B2 | 8/2003 | Bobroff et al. |
| 5,913,846 A | 6/1999 | Szabo | 6,607,511 B2 | 8/2003 | Halseth et al. |
| 5,916,199 A | 6/1999 | Miles | 6,613,064 B2 | 9/2003 | Rutynowski et al. |
| 5,919,167 A | 7/1999 | Mulhauser et al. | 6,620,133 B1 | 9/2003 | Steck |
| 5,919,170 A | 7/1999 | Woessner | 6,620,136 B1 | 9/2003 | Pressly, Sr. et al. |
| 5,925,032 A | 7/1999 | Clements | 6,620,140 B1 | 9/2003 | Metzger |
| 5,947,931 A | 9/1999 | Bierman | 6,629,949 B1 | 10/2003 | Douglas |
| 5,947,935 A | 9/1999 | Rinehart et al. | 6,645,181 B1 | 11/2003 | Lavi et al. |
| 5,951,523 A | 9/1999 | Osterlind et al. | 6,645,182 B1 | 11/2003 | Szabo |
| 5,954,643 A | 9/1999 | VanAntwerp et al. | 6,659,982 B2 | 12/2003 | Douglas et al. |
| 5,957,892 A | 9/1999 | Thorne | 6,685,674 B2 | 2/2004 | Douglas et al. |
| 5,968,011 A | 10/1999 | Larsen et al. | 6,699,218 B2 | 3/2004 | Flaherty et al. |
| 5,975,120 A | 11/1999 | Novosel | 6,702,779 B2 | 3/2004 | Connelly et al. |
| 5,980,488 A | 11/1999 | Thorne | 6,726,649 B2 | 4/2004 | Swenson et al. |
| 5,980,506 A | 11/1999 | Mathiasen | 6,736,797 B1 | 5/2004 | Larsen et al. |
| 5,984,224 A | 11/1999 | Yang | 6,749,587 B2 | 6/2004 | Flaherty |
| 5,984,897 A | 11/1999 | Peterson et al. | 6,749,589 B1 | 6/2004 | Douglas et al. |
| D417,733 S | 12/1999 | Howell et al. | 6,755,805 B1 | 6/2004 | Reid |
| 6,017,328 A | 1/2000 | Fischell et al. | 6,776,775 B1 | 8/2004 | Mohammad |
| 6,017,598 A | 1/2000 | Kreischer et al. | 6,790,199 B1 | 9/2004 | Gianakos |
| D421,119 S | 2/2000 | Musgrave et al. | 6,805,686 B1 | 10/2004 | Fathallah et al. |
| 6,024,727 A | 2/2000 | Thorne et al. | 6,808,506 B2 | 10/2004 | Lastovich et al. |
| 6,039,629 A | 3/2000 | Mitchell | 6,811,545 B2 | 11/2004 | Vaillancourt |
| 6,042,570 A | 3/2000 | Bell et al. | 6,814,720 B2 | 11/2004 | Olsen et al. |
| 6,045,533 A | 4/2000 | Kriesel et al. | 6,824,530 B2 | 11/2004 | Wagner et al. |
| 6,045,534 A | 4/2000 | Jacobsen et al. | 6,824,531 B1 | 11/2004 | Zecha, Jr. et al. |
| 6,050,976 A | 4/2000 | Thorne et al. | 6,830,562 B2 | 12/2004 | Mogensen et al. |
| 6,053,893 A | 4/2000 | Bucher | 6,837,877 B2 | 1/2005 | Zurcher |
| 6,053,930 A | 4/2000 | Ruppert | 6,837,878 B2 | 1/2005 | Smutney et al. |
| 6,056,718 A | 5/2000 | Funderburk et al. | 6,840,922 B2 | 1/2005 | Nielsen et al. |
| 6,056,726 A | 5/2000 | Isaacson | 6,880,701 B2 | 4/2005 | Bergeron et al. |
| 6,074,369 A | 6/2000 | Sage et al. | 6,923,791 B2 | 8/2005 | Douglas |
| 6,074,371 A | 6/2000 | Fischell | 6,926,694 B2 | 8/2005 | Marano-Ford et al. |
| 6,077,244 A | 6/2000 | Botich et al. | 6,939,331 B2 | 9/2005 | Ohshima |
| 6,079,432 A | 6/2000 | Paradis | 6,949,084 B2 | 9/2005 | Marggi et al. |
| 6,086,008 A | 7/2000 | Gray et al. | 6,959,812 B2 | 11/2005 | Reif et al. |
| 6,086,575 A | 7/2000 | Mejslov | 6,960,193 B2 | 11/2005 | Rosenberg |
| 6,090,068 A | 7/2000 | Chanut | 6,979,316 B1 | 12/2005 | Rubin et al. |
| 6,093,172 A | 7/2000 | Funderburk et al. | 6,991,619 B2 | 1/2006 | Marano-Ford et al. |
| 6,093,179 A | 7/2000 | O'Hara et al. | 6,991,620 B2 | 1/2006 | Marano-Ford et al. |
| 6,099,503 A | 8/2000 | Stradella | 6,994,213 B2 | 2/2006 | Giard et al. |
| 6,105,218 A | 8/2000 | Reekie | 6,997,907 B2 | 2/2006 | Safabash et al. |
| 6,106,498 A | 8/2000 | Friedli et al. | 7,014,625 B2 | 3/2006 | Bengtsson |
| 6,120,482 A | 9/2000 | Szabo | 7,018,344 B2 | 3/2006 | Bressler et al. |
| 6,123,690 A | 9/2000 | Mejslov | 7,022,108 B2 | 4/2006 | Marano-Ford et al. |
| 6,132,755 A | 10/2000 | Eicher et al. | 7,047,070 B2 | 5/2006 | Wilkenson et al. |

| Patent/Publication | Date | Name |
|---|---|---|
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,569,262 B2 | 8/2009 | Szabo et al. |
| 7,648,494 B2 * | 1/2010 | Kornerup et al. .............. 604/539 |
| 7,766,867 B2 * | 8/2010 | Lynch et al. ................ 604/93.01 |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer et al. |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |

| | | | |
|---|---|---|---|
| 2006/0036214 A1 | 2/2006 | Mogensen et al. | |
| 2006/0041224 A1 | 2/2006 | Jensen | |
| 2006/0069351 A9 | 3/2006 | Safabash et al. | |
| 2006/0069382 A1 | 3/2006 | Pedersen | |
| 2006/0069383 A1 | 3/2006 | Bogaerts et al. | |
| 2006/0095003 A1 | 5/2006 | Marano-Ford et al. | |
| 2006/0095014 A1 | 5/2006 | Ethelfeld | |
| 2006/0106346 A1 | 5/2006 | Sullivan et al. | |
| 2006/0129123 A1 | 6/2006 | Wojcik | |
| 2006/0135908 A1 | 6/2006 | Liniger et al. | |
| 2006/0135913 A1 | 6/2006 | Ethelfeld | |
| 2006/0142698 A1 | 6/2006 | Ethelfeld | |
| 2006/0161108 A1 | 7/2006 | Mogensen et al. | |
| 2006/0173410 A1 | 8/2006 | Moberg et al. | |
| 2006/0173413 A1 | 8/2006 | Fan | |
| 2006/0184104 A1 | 8/2006 | Cheney, II et al. | |
| 2006/0184140 A1 | 8/2006 | Okiyama | |
| 2006/0200073 A1 | 9/2006 | Radmer et al. | |
| 2006/0241551 A1 | 10/2006 | Lynch et al. | |
| 2006/0247553 A1 | 11/2006 | Diermann et al. | |
| 2006/0247574 A1 | 11/2006 | Maule et al. | |
| 2006/0253085 A1 | 11/2006 | Geismar et al. | |
| 2006/0253086 A1 | 11/2006 | Moberg et al. | |
| 2006/0264835 A1 | 11/2006 | Nielsen et al. | |
| 2006/0264890 A1 | 11/2006 | Moberg et al. | |
| 2007/0005017 A1 | 1/2007 | Alchas et al. | |
| 2007/0016129 A1 | 1/2007 | Liniger et al. | |
| 2007/0016159 A1 | 1/2007 | Sparholt et al. | |
| 2007/0021729 A1 | 1/2007 | Mogensen et al. | |
| 2007/0049865 A1 | 3/2007 | Radmer et al. | |
| 2007/0049870 A1 | 3/2007 | Gray et al. | |
| 2007/0066955 A1 | 3/2007 | Sparholt et al. | |
| 2007/0088271 A1 | 4/2007 | Richards et al. | |
| 2007/0093754 A1 | 4/2007 | Mogensen | |
| 2007/0104596 A1 | 5/2007 | Preuthun et al. | |
| 2007/0112301 A1 | 5/2007 | Preuthun et al. | |
| 2007/0112303 A1 | 5/2007 | Liniger | |
| 2007/0129688 A1 | 6/2007 | Scheurer et al. | |
| 2007/0173767 A1 | 7/2007 | Lynch et al. | |
| 2007/0179444 A1 | 8/2007 | Causey et al. | |
| 2007/0185441 A1 | 8/2007 | Fangrow, Jr. | |
| 2007/0191772 A1 | 8/2007 | Wojcik | |
| 2007/0191773 A1 | 8/2007 | Wojcik | |
| 2007/0203454 A1 | 8/2007 | Shermer et al. | |
| 2007/0213673 A1 | 9/2007 | Douglas | |
| 2007/0244448 A1 | 10/2007 | Lastovich et al. | |
| 2008/0312601 A1 | 12/2008 | Cane | |
| 2010/0004597 A1 | 1/2010 | Gyrn et al. | |
| 2010/0137829 A1* | 6/2010 | Nielsen et al. | 604/506 |
| 2010/0228226 A1* | 9/2010 | Nielsen | 604/506 |

FOREIGN PATENT DOCUMENTS

| | | | |
|---|---|---|---|
| DE | 196 31 921 A1 | 3/1997 | |
| DE | 299 05 072 U1 | 9/1999 | |
| DE | 101 17 285 A1 | 11/2002 | |
| DE | 203 20 207 U1 | 11/2004 | |
| EP | 0117632 B1 | 9/1984 | |
| EP | 0239244 B1 | 2/1987 | |
| EP | 0272530 A2 | 6/1988 | |
| EP | 0451040 A1 | 10/1991 | |
| EP | 0544837 B1 | 6/1993 | |
| EP | 0615768 A2 | 9/1994 | |
| EP | 0651662 B1 | 5/1995 | |
| EP | 0652027 A1 | 5/1995 | |
| EP | 0657184 A1 | 6/1995 | |
| EP | 0688232 B1 | 12/1995 | |
| EP | 0714631 B1 | 6/1996 | |
| EP | 0744183 A2 | 11/1996 | |
| EP | 0747006 A1 | 12/1996 | |
| EP | 0775501 B1 | 5/1997 | |
| EP | 0799626 A1 | 10/1997 | |
| EP | 0937475 A2 | 8/1999 | |
| EP | 0956879 A1 | 11/1999 | |
| EP | 1086718 A1 | 3/2001 | |
| EP | 1125593 A1 | 8/2001 | |
| EP | 0775501 B1 | 6/2002 | |
| EP | 1329233 A1 | 7/2003 | |
| EP | 1350537 A1 | 10/2003 | |
| EP | 1360970 A1 | 11/2003 | |
| EP | 1380315 A1 | 1/2004 | |
| EP | 1407747 A1 | 4/2004 | |
| EP | 1407793 A1 | 4/2004 | |
| EP | 1421968 A2 | 5/2004 | |
| EP | 1177802 B1 | 9/2004 | |
| EP | 1475113 A1 | 11/2004 | |
| EP | 1495775 A1 | 1/2005 | |
| EP | 1502613 A1 | 2/2005 | |
| EP | 1525873 A1 | 4/2005 | |
| EP | 1527792 A1 | 5/2005 | |
| EP | 1616594 A1 | 1/2006 | |
| EP | 1704889 A1 | 9/2006 | |
| EP | 1762259 A1 | 3/2007 | |
| EP | 1764125 A1 | 3/2007 | |
| FR | 2725902 A1 | 10/1994 | |
| FR | 2 752 164 A1 | 2/1998 | |
| GB | 906574 | 9/1962 | |
| GB | 2 088 215 A | 6/1982 | |
| GB | 2 230 702 A | 10/1990 | |
| JP | 10179734 A | 8/1991 | |
| JP | 7051251 A | 11/1995 | |
| JP | 8187286 A | 7/1996 | |
| JP | A-03-191965 A | 7/1998 | |
| JP | 2002-028246 A | 1/2002 | |
| WO | WO 81/01795 A1 | 7/1981 | |
| WO | WO 82/03558 A1 | 10/1982 | |
| WO | WO 92/04062 A1 | 3/1992 | |
| WO | WO 93/05840 A2 | 4/1993 | |
| WO | WO 93/11709 A1 | 6/1993 | |
| WO | WO 94/20160 A1 | 9/1994 | |
| WO | WO 96/32981 A1 | 7/1996 | |
| WO | WO 96/20021 A1 | 10/1996 | |
| WO | WO 98/26835 A1 | 6/1998 | |
| WO | WO 98/33549 A1 | 8/1998 | |
| WO | WO 98/58693 A1 | 12/1998 | |
| WO | WO 99/07435 A1 | 2/1999 | |
| WO | WO 99/33504 A1 | 7/1999 | |
| WO | WO 00/02614 A1 | 1/2000 | |
| WO | WO 00/13757 A1 | 3/2000 | |
| WO | WO 00/44324 A1 | 8/2000 | |
| WO | WO 01/30419 A2 | 5/2001 | |
| WO | WO 01/68180 A1 | 9/2001 | |
| WO | WO 01/72353 A2 | 10/2001 | |
| WO | WO 01/76684 A1 | 10/2001 | |
| WO | WO 01/93926 A2 | 12/2001 | |
| WO | WO 02/02165 A2 | 1/2002 | |
| WO | WO 02/07804 A1 | 1/2002 | |
| WO | WO 02/40083 A2 | 5/2002 | |
| WO | WO 02/053220 A2 | 7/2002 | |
| WO | WO 02/068014 A2 | 9/2002 | |
| WO | WO 02/081012 A2 | 10/2002 | |
| WO | WO 02/081013 A2 | 10/2002 | |
| WO | WO 02/083206 A2 | 10/2002 | |
| WO | WO 02/094352 A2 | 11/2002 | |
| WO | WO 02/100457 A2 | 12/2002 | |
| WO | WO 02/102442 A1 | 12/2002 | |
| WO | WO 03/015860 A1 | 2/2003 | |
| WO | WO 03/026728 A1 | 4/2003 | |
| WO | WO 03/068305 A1 | 8/2003 | |
| WO | WO 03/075980 A2 | 9/2003 | |
| WO | WO 03/095003 A1 | 11/2003 | |
| WO | WO 2004/012796 A1 | 2/2004 | |
| WO | WO 2004/029457 A1 | 4/2004 | |
| WO | WO 2004/030726 A1 | 4/2004 | |
| WO | WO 2004/037325 A1 | 5/2004 | |
| WO | WO 2004/054644 A1 | 7/2004 | |
| WO | WO 2004/056412 A2 | 7/2004 | |
| WO | WO 2004/064593 A2 | 8/2004 | |
| WO | WO 2004/071308 A1 | 8/2004 | |
| WO | WO 2004/087240 A1 | 10/2004 | |
| WO | WO 2004/098683 A1 | 11/2004 | |
| WO | WO 2004/101016 A1 | 11/2004 | |
| WO | WO 2004/101071 A2 | 11/2004 | |
| WO | WO 2004/110527 A1 | 12/2004 | |
| WO | WO 2005/002649 A1 | 1/2005 | |
| WO | WO 2005/004973 A1 | 1/2005 | |
| WO | WO 2005/018703 A2 | 3/2005 | |
| WO | WO 2005/037184 A2 | 4/2005 | |
| WO | WO 2005/037350 A2 | 4/2005 | |

| | | | |
|---|---|---|---|
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A1 | 8/2007 |
| WO | WO 2007/122207 A1 | 11/2007 |
| WO | WO 2007/140631 A1 | 12/2007 |
| WO | WO 2007/140783 A1 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/034830 A1 | 4/2010 |

OTHER PUBLICATIONS

"Why inset®?" inset® infusion set product overview; http://web.archive.org/web/20040906102448/http://www.infusion-set.com/Default.asp?ID=108; two pages.

* cited by examiner

INFUSION SET

This application claims the benefit under 35 U.S.C. §371 of International Application No. PCT/DK2007/000459, filed Oct. 29, 2007, which claims the benefit of European Patent Application No. 06 022 674.3, filed Oct. 31, 2006, and U.S. Provisional Application Ser. No. 60/855,554, filed Oct. 31, 2006. These references are incorporated herein in their entirety.

FIELD OF INVENTION

The invention relates to an infusion set for an intermittent or continuous administration of a therapeutic substance, such as insulin. Further the invention relates to a kit comprising an injector device and an infusion set.

An infusion set comprises an infusion part with a cannula to penetrate the skin of a person and a connector for connecting the infusion part with a medical device, preferably a medical device such as an insulin pump. An infusion set has in its assembled form a substantially planar rear side and a relatively large width compared to its thickness, thus allowing it to lie flat on the patient's skin and thereby minimizing the discomfort of carrying the infusion set.

The infusion part is placed stationary on the patient for a longer and not specified period of time while the connector is supposed to be connected and disconnected from time to time. Hereby it is possible for the patient to disconnect from a medical device such as a pump connected to a reservoir of medication, move around and at a later point re-connect to the medical device. Further it is possible to shift between different medical devices e.g. different reservoirs of medication, using the same infusion part and only requiring one penetration of the skin and providing less discomfort to the patient.

Some people are reluctant or hesitant to pierce their own skin with a medical needle, and thus encounter difficulties in correct needle or cannula placement for proper administration of the medication. Therefore it is possible to use an injector device for the placement of the infusion set into the skin of a patient.

BACKGROUND OF THE INVENTION

WO2005/092410A1 describes an infusion set for intermittent or continuous administration of a therapeutically substance, such as insulin, comprising an infusion part for insertion into a patient and a connector for connecting the infusion part with a medical device through a tube, the connector being axially displaceable relative to the infusion part. The infusion part comprises an adhesive support, a base part with a first set of guiding means and at least two retention devices for locking the connector to the infusion part, a cannula extending from said base part and being in fluid communication with a cavity. The cavity is further adapted to receive a second cannula extending from the connector, which second cannula is in fluid communication with the tube. The connector also comprises at least two arms comprising means corresponding to the retention devices extending from the base part.

The coupling mechanism between the infusion part and the connector of this infusion set is quite strong when the arms are in a locked position The risk/chance of pulling the connector away from the infusion part when positioned on the skin of the patient is negligible for this known infusion set, as the device has front-facing arms and corresponding retention devices.

When a patient accidentally pulls or overloads the tube extending from the infusion set via the connector by pulling the tube in an upward direction, this results in the connector being tilted relative to the infusion part thereby tightening the engagement between the retention devices on the infusion part and the corresponding retention devices on the two arms of the connector. In this way, the strong coupling mechanism between the connector and the infusion part will result in both the connector and the infusion part not being able to disconnect from each other when the connector or the tube of the connector is being overloaded or pulled in an upward direction but resulting in the whole infusion set being pulled out of the patient's skin. The patient will then have to re-inject a new infusion set with the resulting discomfort.

Accordingly, it is an object of the invention to provide an infusion set having a coupling mechanism between the infusion part and the connector which coupling mechanism separates the connector from the infusion part when the infusion set is being exposed to overload or accidental pulling of the tube extending from the connector.

It is another object of the invention to provide an infusion set with a clear view of the insertion site.

SUMMARY OF THE INVENTION

In a first aspect the present invention relates to an infusion set for intermittent administration of a therapeutically substance through the skin of a patient, comprising an infusion part having a base part with a main plane, a head part extending from the main plane of the base part and having a cannula extending from the base part into the skin of a patient, first fastening means for fastening the infusion part to the skin of a patient, a connector having a plane being parallel to and above the main plane of the base part, and having one or more arms, said arms being fastened to the connector at a first end, and being free in a second opposite end, and a tube for connecting the infusion set to a medical device, guide means for positioning the infusion part and the connector in relation to each other, second fastening means for fastening the connector to the infusion part, the second fastening means being in the form of connector retention devices positioned on the arms of the connector adapted to engage with corresponding retention devices extending from the base part, wherein the plane of the connector can be tilted to a distance from the base plate, causing the second end to be displaced to a distance that is larger than the height of the retention devices, said retention devices being positioned in the second end of the base part, when the connector is positioned via the guide means relative to the infusion part.

Further, the connector is pivotable at the first end when position in the guide means around an axis, said axis being parallel to the main plane of the base part and perpendicular to a longitudinal axis A of the infusion part.

It has surprisingly been shown, that the above described infusion set will seem safer to use for the patient than the previously known infusion sets as the infusion part, when the force for disconnecting the connector from the infusion part is less than the force for removing the infusion part from the skin of a patient, will disconnect from the connector, when the connector is being pushed or pulled away in an inclined motion from the infusion part e.g. by an accidental pull of the tube.

Furthermore, the infusion set can be constructed for an inclined insert, where the cannula can extend from the first end of the base part or head part essentially along a longitudinal axis A or slightly angled in relation to the axis A, in order to provide the patient with an infusion set with an inclined insert in a manner known per se. The infusion set can also be constructed for an insert perpendicular to the skin surface, when mounted into the skin of a patient, where the cannula extends from a lower surface of the base part and perpendicular to said base part.

When the infusion set is positioned on the skin of a patient, e.g. perpendicular to the skin surface of the patient, the infusion set covers the needle insertion site. In order to get a clear view of the insertion site without removing the infusion part, the head part extending from the base part of the infusion part can be provided with a see-through part. This see-through part can be formed in various ways such as by casting the head part in a transparent polypropylene, by reducing the thickness of the head part or by providing the head part with a magnifying area and the like.

This ensures a good and clear view of the insertion site whereby it is possible to check the insertion site including that the insertion site is clean and not infected together with the cannula being positioned into the skin of the patient in the right position.

In a second aspect the invention relates to a kit comprising an injector device and an infusion set according to the invention where the injector device comprises a housing, a plunger slidably received within the housing for movement between an advanced position and a retracted position, the plunger having substantially non-detachably secured thereto an insertion needle for receiving and supporting the cannula of the subcutaneous infusion set in a position with the cannula, where the insertion needle is removable from the cannula while maintaining a transcutaneous placement of the cannula, a drive for urging the plunger from the retracted position toward the advanced position to transcutaneously place said cannula of the subcutaneous infusion set received on the insertion needle.

The above mentioned kit is designed to place the cannula of the infusion set with the insertion needle extending there through to ensure proper needle placement with minimal patient discomfort. The injector device may also allow placement of the insertion needle through the skin at a selected insertion angle. After priming and placement of the infusion set the injector device is removed and delivery of medication is initiated. The kit comprising the injector device and the infusion set is normally provided to the patient as a sterile sealed single use assembly.

BRIEF DESCRIPTION OF THE DRAWINGS

In the following the invention will be described in further details with reference to the accompanying drawings.

FIG. 8*a* shows different shapes of connector retention devices on the connector.

DETAILED DESCRIPTION

The invention is explained more in detail with reference to the drawings showing an embodiment of the invention.

Infusion Set

Figures 1, 3:
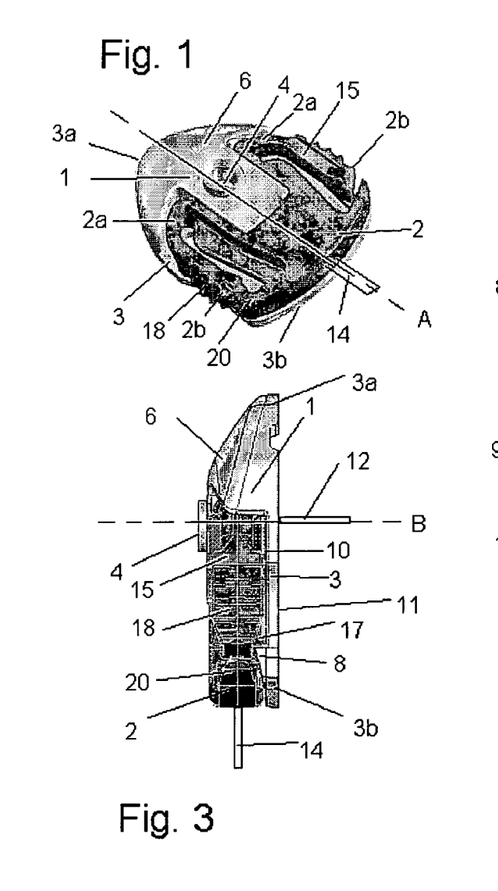
FIG. 1 shows an embodiment of an infusion set where the infusion part and the connector are unified.
FIG. 3 shows a side view of the same embodiment of an infusion set shown in FIG. 1.
Figure 2:
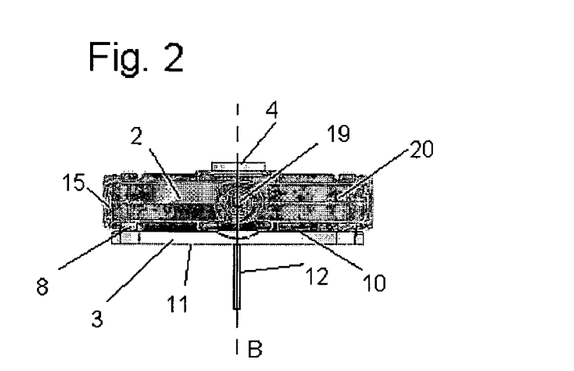
FIG. 2 shows an end view of the same embodiment of an infusion set shown in FIG. 1.

FIG. 1-7 illustrates an embodiment of an infusion set for intermittent administration of a therapeutically substance through the skin of a patient, where the infusion set comprises an infusion part 1 and a connector 2 for connecting the infusion part 1 with a medical device (not shown) through a tube 14 extending through an opening 19 in the connector 2, as can be seen in FIG. 2. The connector 2 and the infusion part 1 is having a longitudinal axis A, said connector 2 being axially displaceable along said longitudinal axis A relative to the infusion part 1.

Infusion Part

Figure 4:
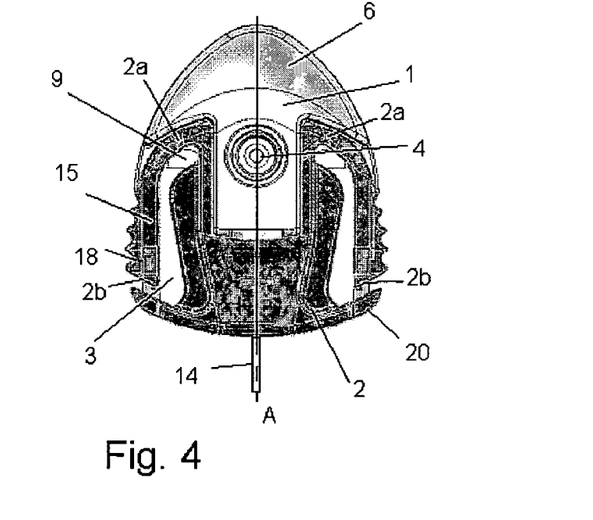
FIG. 4 shows a top view of the same embodiment of an infusion set shown in FIG. 1.
Figure 5:
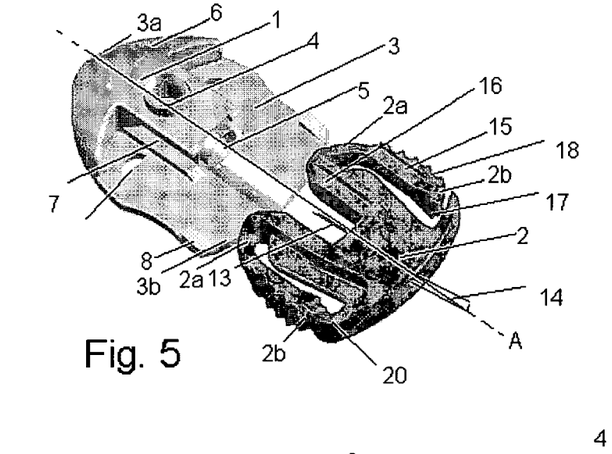
FIG. 5 shows an embodiment of the infusion set where the infusion part and the connector are separated.
Figure 6:
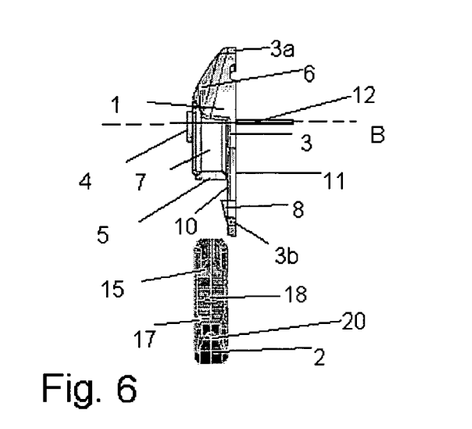
FIG. 6 shows a side view of the same embodiment of an infusion set shown in FIG. 5.
Figure 7:
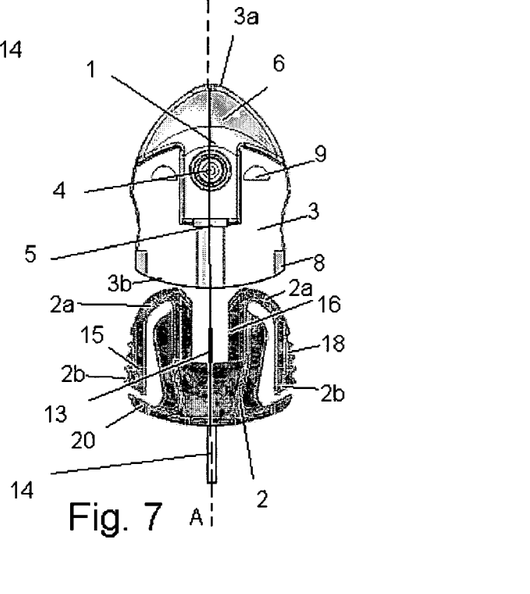
FIG. 7 shows a top view of the same embodiment of an infusion set shown in FIG. 5.

As can most clearly be seen in FIGS. 5-7, the infusion part 1 comprises a base part 3 with a main plane being essentially parallel to the skin of the patient, when the infusion set is attached to a patient, said base part having a first surface 10 and a second surface 11, the second surface 11 being closest to the skin of a patient and being provided with a first fastening means for fastening the infusion part 1 to the skin of a patient and a head part 6 extending from the first surface, i.e. the main plane, of the base part 3, said head part 6 having a cannula 12 extending from the base part 3 into the skin of a patient. In this embodiment, as shown in FIGS. 5-7, the cannula 12 is extending from the second surface 11 of the base part thereby penetrating the first fastening means. Alternatively the cannula 12 can extend from the head part or the base part 3 of the infusion part 1 essentially along the axis A for an inclined insertion of the cannula 12. Furthermore, the infusion part comprises guide means 7 for positioning the infusion part 1 and the connector 2 in relation to each other these guide means 7 of the infusion part 1 being positioned on the head part 6. As can be seen in FIGS. 1, 3 and 5, the base part 3 has a first end 3*a* and an opposite second end 3*b*, the first end 3*a* being the end provided with the head part 6 and the second end 3*b* being positioned opposite the first end 3*a*. The base part 3 can be divided into three parts, the first part incorporating the first end 3*b* and normally being covered with the head part 6, the middle part normally being provided with a needle insertion opening 4 and the last third incorporating the second opposing end 3*b* normally being provided with retention devices 8. As shown in FIGS. 4, 5, and 7, the base part 3 is further provided with openings 9, in this case two openings 9, placed between the head part 6 and the retention devices 8. In this embodiment these two openings 9 are related to manufacturing purposes.

First Fastening Means

Figure 9:
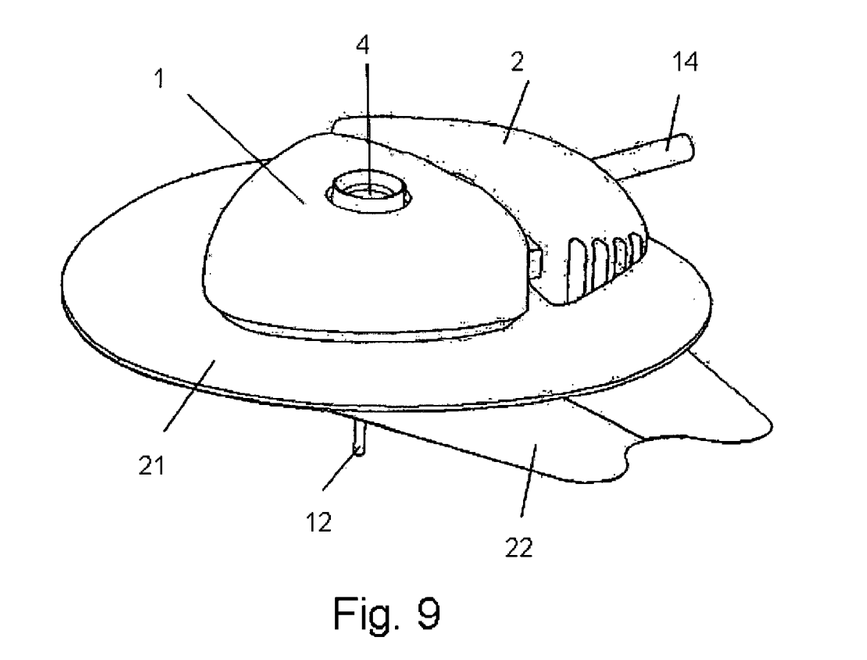
FIG. 9 shows an embodiment of the infusion set including a mounting pad in accordance with the invention.

In one embodiment, as illustrated in FIG. 9, the first fastening means could be in the form of a mounting pad 21 for attaching the infusion part 1 to the skin of a patient comprises an adhesive layer (not shown) and a removable release liner 22, which covers the adhesive layer. In general the adhesive layer is a skin friendly adhesive known per se. The mounting pad may be a dressing, a plaster, an adhesive pad or the like and may be configured in various shapes such as circular, oval, triangular, rectangular etc.

Connector

As most clearly seen in FIGS. 5-7, the connector 2 has a plane being parallel to and above the main plane of the base part 3 when assembled with the infusion part 1. In this embodiment as clearly illustrated in FIGS. 1, 4, 5 and 7, the connector is provided with two arms 15, which arms are fastened to the connector 2 at a first end 2a, and unfastened and free in a second opposite end 2b, so that the arms 15 can move laterally at the second end 2b. The second end 2b of the connector 2 corresponds to the second end 3b of the base part 3, when the infusion part 1 and the connector 2 are positioned and assembled relative to each other. By providing the connector with two arms 15 it is easier to get a good grip and a better control over the connector 2, when the connector 2 is to be disconnected from the infusion part 1 intended.

As can be seen in e.g. FIG. 5-7 the connector 2 is further provided with a protecting part 20 for protection of the free second end 2b of the arms 15, the arms 15 being more flexible at the free second end 2b, and therefore more sensitive to contact at the free second end 2b, in order not to release or disconnect the connector 2 from the infusion part 1 unintended by accident. As mentioned above, the connector comprises the tube 14 positioned in the second end 2b for connecting the infusion set to a medical device. Furthermore, the connector comprises guide means 16 for positioning the infusion part 1 and the connector 2 in relation to each other. The connector 2 can be symmetrically formed around a connector main plane and around the plane perpendicular to the main plane and parallel to the main axis, which allows the connector 2 to match with the base part 3 in two ways.

Flow Path

As can be seen in FIGS. 1-7 the head part 6 of the infusion part 1 is further provided with an insertion needle opening 4 for receiving an insertion needle for insertion of the infusion device, and a connector opening 5 for receiving a second cannula 13, which second cannula 13 is extending from the connector 2 along the longitudinal axis A. This cannula 13 is in fluid connection with the tube 14 extending from the opening 19 in the connector 2, which tube 14 provides the connection to a medical device such as an insulin pump (not shown). In the alternative, as the insertion needle opening 4 is provided for the insertion of a soft cannula 12, the head part 6 need not be provided with an insertion needle opening 4 if the cannula 12 is made of metal. The head part 6 is provided with a cavity (not shown), which cavity is adapted for receiving both the cannula 12 and the second cannula 13, said cannula 12 being in fluid communication with said cavity, and the second cannula 13, which extends along a longitudinal axis A from the connector 2, is being in fluid communication with the tube 14, i.e. cavity as used herein designates the inner lumen of the cannula or the extension of the cannula. The cavity is being positioned in the head part 6 between the first set of guide means 7 and limited by the first surface 10 of the base plate, the insertion needle opening 4 as well as the connector opening 5. I.e. the cavity (not shown) optionally being covered by a membrane is adapted to receive the second cannula 13 extending from the connector 2.

In this embodiment, as shown in FIGS. 2, 3 and 6, the cannula 12 is extending from the second surface 11 of the base part 3 along a longitudinal axis B thereby being positioned perpendicular to the skin of the patient. In the alternative, the cannula 12 can extend from the first end 3a of the base part or head part 6 essentially along the axis A or slightly angled in relation to the axis A in order to provide the patient with an infusion set with an inclined insert in a manner known per se as described in WO 94/20160.

Guide Means

As illustrated in e.g. FIG. 5 and as mentioned in the sections infusion part and connector above, the infusion part 1 and the connector 2 are each provided with corresponding guide means 7,16 for positioning and aligning the infusion part 1 and the connector 2 in relation to each other. The guide means can be in the form of a tongue and groove mechanism. The tongue and groove mechanism can be of different configurations or shapes, for instance it may be in the form of a pater/mater system or the tongue and groove may be formed with a triangular or semi-cylindrical cross sectional area. In this embodiment the first guide means 7 of the infusion part 1 is having the form of two grooves placed symmetrically around the main plane of the base part 3, these grooves 7 being adapted to engage with a second set of corresponding guide means 16 placed on the connector 2, in this embodiment the corresponding second guide means 16 are in the form of two tongues or projecting parts, such as stabilizing fins which fit within the first guide means 7, the guide means 7,16 thereby constituting a tongue and groove system. As an alternative, the first guiding means 7 of the infusion part 1 could be in the form of projecting fins and the second guide means 16 on the connector 2 could be in the form of recesses or grooves.

Second Fastening Means—Retention Devices

The infusion part 1 and the connector 2 are provided with second fastening means for fastening the connector 2 to the infusion part 1. As can be seen in e.g. FIG. 5, the second fastening means are in the form of connector retention devices 17 positioned on the free end of the arms 15 of the connector 2 adapted to engage with corresponding retention devices 8 positioned in the second end 3b on the base part 3 of the infusion part 1. In this way, the connector 2 is releasably fastened to the infusion part 1.

When the infusion part 1 and the connector 2 are assembled, the free end of the arms 15, i.e. the second opposite end 2b, is positioned just opposite or above the retention devices 8 in the second end 3b of the base part 3. As shown in FIG. 5-7 the retention devices 8 in this embodiment are two retention devices 8 extending from the first surface 10 of the base part 3 for fastening or retention of the connector 2 to the infusion part 1. In this embodiment the retention devices 8 are placed on the far rear end, meaning the second end 3b, of the base part 3 and the connector retention devices 17 of the rear-facing arms 15 are likewise placed on the far rear end, meaning the second end 2b, of the rear-facing arms 15 corresponding to the retention devices 8.

Accidents involving pulling or tugging in an inclined motion of the tube extending from the connector 2, due to e.g. the tube catching on to something, thereby overloading the infusion set often happens resulting in the infusion set being unintentionally pulled from the skin of the patient. It is essential for the user that at least the infusion part 1 of the infusion set 1,2 remains in place after insertion even when accidents involving pulling or tugging of the tube is involved. The present invention complies with this purpose as the plane of the of the connector 2 can be tilted to a distance from the base plate 3, causing the second end 2b to be displaced to a distance that is larger than the height (h) of the retention devices 8, said retention devices 8 being positioned in the second end 3b of the base part 3, when the connector 2 is positioned via the guide means 7,16 relative to the infusion part 1. As the plane of the connector 2 is displaced, i.e. being inclined from the base part 3, the second end 2b of the connector together with the arms 15 of the connector will be lifted resulting in the connector retention devices 17 being freed from the retention devices 8. Hereby the retention devices 8 and the connector retention devices 17 will be released from each other resulting in the connector 2 disconnecting from the infusion part 1 as opposed to the infusion part 1 being peeled of the skin of the patient.

In an embodiment of the invention, the second end 2*b* of the connector 2 can be displaced to a distance from the base plate 3, which distance is larger than the height (h) of the retention devices 8, by making the connector 2 pivot around a point in the guide means 7, 16.

Retention Devices

As mentioned above, the displacement of the connector 2 from the main plane of the base plate 3, when the connector 2 is positioned via the guide means 7, 16 relative to the infusion part 1, is dependent on the height of the retention devices 8 and the height (h) of the connector retention devices 17. The lower the height of the retention devices 8 and the connector retention devices 17, the less displacement of the second end 2*b* from the main plane of the base part 3 is needed for releasing the connector 2 from the infusion part 1. The height of the retention devices 8 is again dependent on the shape of the retention devices 8 and the connector retention devices 17 including the contact surface of both the retention devices 8, 17.

Figure 8:
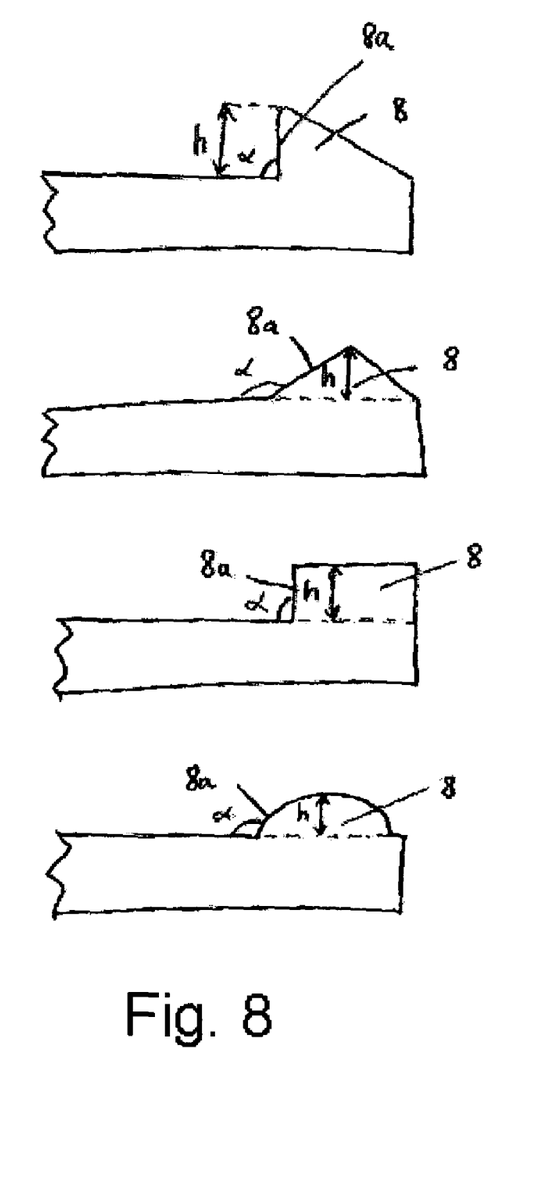
FIG. 8 shows different shapes of retention devices on the base part.

In FIG. 8 different shapes of the retention devices 8 are illustrated. The retention devices 8 are formed with a contact surface 8*a* for contact with the opposing contact surface 17*a* of the corresponding connector retention devices 17 of the arms 15, which opposing contact surface 17*a* can be seen in FIG. 8*a*. The contact surface 8*a* of the retention devices 8 is extending from the first surface of the base part 3. The contact surfaces 8*a* have a plane having a projection of the height (h) perpendicular to the main plane of the base part 3. In one embodiment the contact surface 8*a* of the retention devices 8 is being essentially perpendicular to the main plane of the base part 3, when the infusion part 1 and the connector 2 are connected, i.e. the angle between the contact surface 8*a* and the base part 3 is approximately 90°. However, the form of the retention devices 8 could also be e.g. as a slope, a chute, a half-circle, a triangle or the like, where the contact surface 8*a* is being angled relative to the main plane of the base part 3, i.e. that the angle α between the contact surface 8*a* of the retention devices 8 and the base part 3 is more than 90° as can be seen in FIG. 8. For each of the mentioned shapes of the retention devices 8 the projection of the height (h) perpendicular to the main plane of the base part 3 can be varied. In this way, it is possible to vary the height of the retention devices 8 on the base part 3 and thereby influence the slipping between the two contact surfaces of the retention devices 8 and the connector retention devices 17 so as to secure that the connector 2 is disconnected from the infusion part 1, when the tube 14 is accidentally pulled in an inclined motion.

Other shapes than the shapes shown in FIG. 8 is possible in order to obtain the height of the retention devices 8 which is required or needed for disconnecting the connector 2 from the infusion part 1.

Connector Retention Devices

As shown in FIG. 8*a*, the connector retention devices 17 of the arms 15 of the connector 2 are as the retention devices 8 formed with a corresponding contact surface 17*a* which likewise can be formed as e.g. a slope, a chute, a half-circle, a triangle and the like, by triangle is meant that the retention devices shaped as a right-angled triangle when viewed from the side or having a right-angled triangular cross-section, which interlocks or fasten the arms 15 to the retention devices 8 on the base part 3. For each of the mentioned shapes of the connector retention devices 17 the projection of the height perpendicular to the main plane of the connector 2 can be varied. In this way it is also possible to vary the height (h) of the connector retention devices 17 and influence the slipping between the two contact surfaces of the retention devices 8 and the connector retention devices 17 so as to secure that the connector 2 is disconnected from the infusion part 1, when the tube 14 is accidentally pulled in an inclined motion.

When the infusion part 1 and the connector 2 are assembled, the contact surface 8*a* of the retention devices 8 and the contact surface 17*a* of the connector retention devices 17 are engaged with each other, hereby securing the assembly of the connector 2 and the infusion part 1. Thus, if a pull or a toggle of the tube 14 or of the second end 2*b* of the connector 2 along the axis A is performed, the retention devices 8 and the connector retention devices 17 will not disengage. In order to intended release the connector 2 from the infusion part 1, the arms 15 of the connector will have to be gripped and pressed to displace the arms axial along and axis in the main plane of the connector and perpendicular to the axis A. In this way the connector retention devices 17 on the arms 15 are freed from the retention devices 8 on the base part 3.

Head Part

When the cannula 12 is inserted into the skin of a patient and the insertion angle being perpendicular to the main plane of the base part 3, the head part 6 of the infusion part 1 will normally cover the insertion site. By making the head part 6 of a see-through material such as transparent polypropylene (PP), the head part 6 can function as a window giving the patient or the user a clear view of the place of insertion. By providing a see-through part or a window in the head part 6 of the infusion part 1, the patient or the user therefore can keep the insertion site under observation and at all times determine whether the insertion site or the insertion wound is infected or not or whether the cannula 12 is positioned correctly into the skin of the patient.

Another way of making the head part 6 of the infusion part 1 sufficiently transparent to get a good visual impression and a clear view of the inserted cannula, is to polish the mould used for making the infusion part 1 before casting the infusion part 1. This renders the mould smooth and assists efforts of both the first and second surface of the head part 6 to be transparent. As another alternative, it is possible to cast the infusion part 1 and afterwards polish the head part 6 of the infusion part 1. As further alternative, it is possible to cast the infusion part 1 with a concavity in the second surface of the head part 6, said second part facing the skin of the patient, so that the thickness of the head part 6 above the insertion place/wound area is decreased or reduced providing better see-through properties and increased view through the head part 6. As a still further alternative, it is possible to either produce the infusion part 1 with a magnifying area or a lens embedded in the head part 6 or to fit or mount a lens in the head part 6 of the infusion part 1 during moulding. This way, when looking through the magnifying area or the lens of the head part 6, a magnified view of the insertion place/wound area is generated.

Gripping Means

In an embodiment, as shown in FIG. 5-7, the arms 10 of the connector 2 is provided with gripping means 18 in the form of recesses. The gripping means 18 are optional and can be rims, grooves, scores, recesses and pebbled or roughened surface, optionally of another material than the connector itself. This ensures a more simple and easy grip when gripping and pressing the arms of the connector 2 with the first finger and the thumb for fastening or unfastening of the connector 2 from the infusion part 1.

Materials/Plastics

In another embodiment the infusion part 1 and the connector 2 of the infusion set are made from two different plastics materials, such as two different types of polypropylene. When making the infusion set of different materials it is possible to enhance the different characteristics which are working for each of them. The infusion part 1 is normally quite small and is put in a stationary position during use, which is why it should have a smooth surface and a limited flexibility in order to provide the user with the best comfort. The connector is normally also quite small and is often moved during use, the connector therefore should be easy and comfortable to handle. The infusion part and/or the connector can essentially be made of polypropylene, e.g. such as transparent polypropylene. In this way it is possible to see through the infusion set and thereby being able to see the cannula insertion wound.

Cannula

The cannula 12 is preferably a soft cannula made of a thermoplastic elastomer (TPE), the TPE's being selected from the group consisting of polyester ethers, ECDEL, styrene based TPE, olefin based TPE, urethane based TPE, ester based TPE, amid based TPE, polyolefin sans silicone rubbers such as polypropylene, C-FLEX™, mixtures of C-FLEX™ and polypropylene, LUPOLEN™ 1840H, LUPOLEN™ 3020D, PELLETHANE™ 2362-75D, PELLETHANE™ 2363-55D, TECOTHANE™ and CARBOTHANE™, but could also be made of metal.

Luer Coupling/Medical Device

The connector 2 can be connected to a luer coupling member through the tube 14. Through the luer coupling it is possible to administer a suitable therapeutically substance, such as insulin from a pump. The connector can also be a sort of closing part with a suitable entrance for an inserting needle of a syringe. Such a closing part can stay in position for up till three days while the user can have medication, e.g. insulin injected through the entrance in order to reduce trauma to the skin caused by repeated penetration of the skin.

Kit Comprising an Infusion Set and an Insertion Device

In another embodiment the invention relates to a system or a kit, said kit comprises an injector device together with an infusion set according to the invention. The injector device itself is being provided to the patient as a sterile sealed, single use assembly. The injector device is for quick and easy placement of the infusion set and may then be discarded safely.

Injector Device

Figure 10:
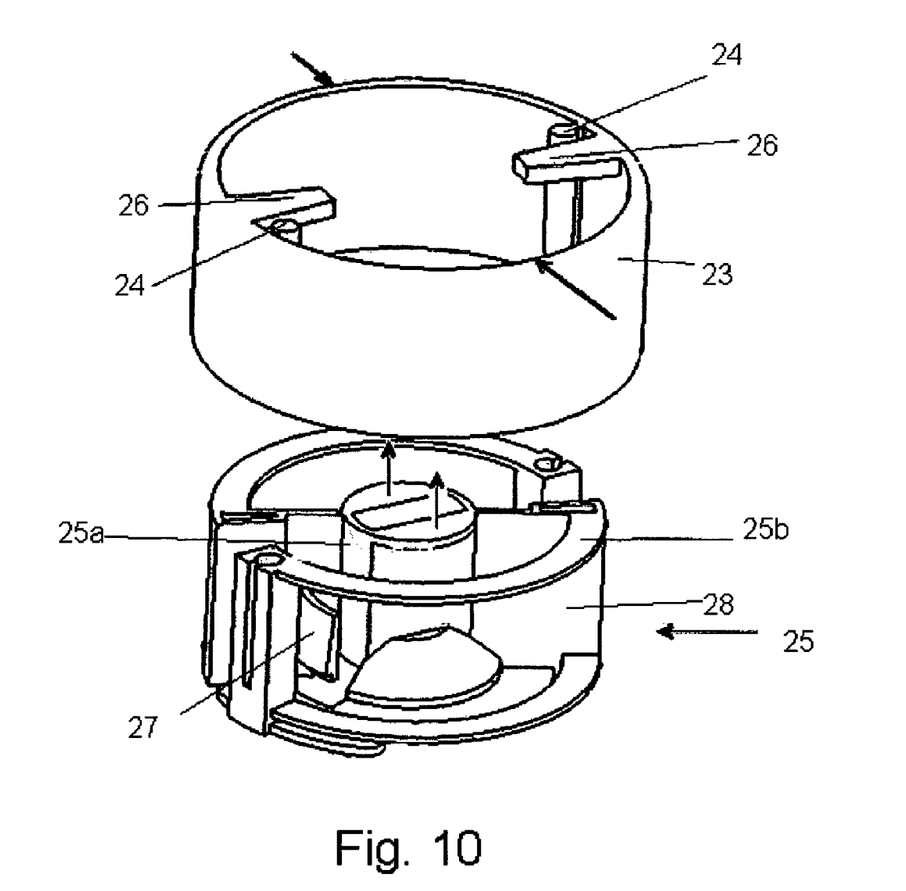
FIG. 10 shows an embodiment of an injection device which can be used with an infusion set in accordance with the invention.

FIG. 10 shows an embodiment of an injector device which can be used with an infusion set in accordance with the invention. The injector device comprises a housing 23, in this embodiment the housing comprises two fastening elements 24 which assures that a plunger 25 cannot rotate in relation to the housing. The plunger 25 is slidably received within the housing 23 for movement between an advanced position and a retracted position, the plunger 25 having substantially non-detachably secured thereto a medical insertion needle (not shown) with a pointed end for receiving and supporting the cannula 12 of the subcutaneous infusion set in a position with the cannula 12, where the insertion needle is removable from the cannula 12 while maintaining a transcutaneous placement of the cannula 12.

By substantially non-detachably as used in the present application is meant a connection, which will remain stable under normal conditions of use to allow the needle to remain on the plunger 25 when retracting the injector device from the patient's skin.

The housing 23 of the injector device can also comprise detaining elements 26 in the form of two protruding parts keeping the plunger 25 in a biased position until the plunger are released from the biased position by affecting some release means. The plunger 25 is constructed with a central part 25a and a surrounding part 25b. The central part 25a functions as a finger grip and the surrounding part 25b functions as a drive. The central part 25a can slide between an advanced position and a retracted position in relation to the housing 23 and the infusion part 1 of the infusion set is fastened to the central part 25a. The surrounding part 25b is constructed as two parts formed almost as semicircles, where one end of each semicircle is attached to one of the fastening elements 24 of the housing 23, and the other end of each semicircle is fastened to the central part 25a. The end of the semicircle fastened to the housing 23 at the fastening elements does not move relative to the housing 23 during use. The other end of the semicircle which is attached to the central part 25a is pulled out of the housing 23 (arrows for direction in FIG. 10). When pulling in the central part 25a, the surrounding part 25b which functions as a drive, will be tightened. The surrounding part 25b is kept in the biased position by two protrusions 27 (only one shown). The protrusions 27 are in this embodiment attached to a connecting wall 28, but could just as well be attached to the central part 25a. When the central part is pulled out of the housing 23, the protrusions 27 will be pulled past the detaining elements 26 and these elements will prevent the protrusion 27 and thereby the central part 25a from returning to a relaxed position inside the housing 23.

The housing 23 can be released by pressing on the sides of the housing at a line perpendicular to the line formed by the two detaining elements 26 (direction indicated by arrows on FIG. 10). When pressing at the two opposite sides in this position, the resulting deformation of the housing will cause the two detaining elements 26 to be pushed away from each other, thereby leaving enough room for the protrusions 27 to pass by the detaining elements 26 and for the central part 25a to be forced back into the relaxed position by the drive in the form of the surrounding part 25b.

The insertion needle may be connected to the plunger 25 in any suitable manner such as in the process of moulding the plunger, or the insertion needle may be press-fit in the plunger 24. The insertion needle may be oriented at an angular position relative to the skin of the patient so as to make an insertion perpendicular to the skin of the patient or so as to make an inclined insertion.

The housing 23 may have a circular, square or any desired cross-sectional shape. The housing 23 and the plunger 24 are advantageously formed of a plastics material in a moulding process.

Other Injector Devices

Other injector devices than described here can be used together with the infusion set according to the invention but it is necessary that it is possible to adapt the infusion part 1 of the infusion set and to keep it in position until insertion has taken place.

Manually Insertion

Whether the infusion set is intended to be inserted manually or by an injector the infusion part 1 and the connector 2 can be delivered to the user as two separate units. When inserted manually the infusion part 1 will at delivery be combined with a needle unit with the same locking and guiding means as the connector. The needle unit is provided with an insertion needle extending from the central front which insertion needle at delivery extends through and beyond the end of the cannula. The needle unit's only function will be to penetrate the user's skin where after the needle unit is removed and replaced with the connector leaving the cannula subcutaneous.

Other Medical Devices

As mentioned above, the connector 2 can be coupled via the tube 14 to a pump for administrating a therapeutically substance such as insulin.

However, the connector 2 can be replaced with a dummy connector or dummy part, which dummy part is shaped to correspond to the connector 2 but without the tube 14 in the second end 2b of the connector 2. In this way, a patient can disconnect the real connector 2 and replace the real connector 2 with said dummy part, a consequence hereof being that the pump for administrating medicines or a therapeutically substance likewise will be disconnected from the patient's infusion set. When the patient is wearing the dummy part or dummy connector and is in need of medication or a therapeutically substance, the patient can e.g. inject the medication or a therapeutically substance through the insertion needle opening 4 in the infusion part 1 directly into the cannula 12 by means of e.g. a syringe.

In this way, it is easier for the patient to leave the house for a shorter period of time without the inconvenience of having to bring unmanageable medical equipment such as the above mentioned pump for administrating medicines, but still be able to inject medicines or a therapeutic substance by use of e.g. a small syringe when needed.

The invention has been described with reference to particular embodiments. Many modifications can be carried out without thereby deviating from the scope of the invention.

The invention claimed is:

1. An infusion set for intermittent administration of a therapeutic substance through the skin of a patient, comprising:
   an infusion part comprising a base part having a main plane, a head part extending from the main plane of the base part and a cannula extending from the base part into the skin of a patient,
   first fastening means for fastening the infusion part to the skin of a patient,
   a connector having a plane parallel to and above the main plane of the base part, and having one or more arms, said arms being fastened to the connector at a first end, and being free in a second opposite end, and a tube positioned in the second end for connecting the infusion set to a medical device,
   a guide means for positioning the infusion part and the connector in relation to each other,
   second fastening means for fastening the connector to the infusion part, said second fastening means comprising projecting connector retention devices positioned on the arms of the connector adapted to engage with retention devices extending from the base part,
   wherein said retention devices of the second fastening means being positioned in a second end of the base part and corresponding to the connector retention device positioned at the free end of the one or more arms of the connector, when the connector is positioned via the guide means relative to the infusion part, and wherein the connector further comprises a protruding protecting part for protection of the free second end of the one or more arms.

2. An infusion set according to claim 1, wherein the connector is pivotable at the first end when positioned in the guide means around an axis, said axis being parallel to the main plane of the base part and perpendicular to a longitudinal axis A of the infusion part.

3. An infusion set according to claim 1, wherein the cannula of the infusion part is extending perpendicular to and from a lower surface of the base part.

4. An infusion set according to claim 1, wherein the contact surface of the connector retention devices of the arms is being essentially perpendicular to the main plane of the base part, when the infusion part and the connector are assembled.

5. An infusion set according to claim 1, wherein the head part of the infusion part comprises transparent polypropylene.

6. An infusion set according to claim 1, wherein the arms of the connector comprise gripping means for easy gripping when pressing the arms for disconnection of the connector from the infusion part.

7. An infusion set according to claim 1, wherein the infusion part and the connector are made from two different plastics materials.

8. An infusion set according to claim 1, wherein the infusion part or the connector consists essentially of polypropylene.

9. An infusion set according to claim 1, wherein the medical device is an insulin pump.

10. An infusion set according to claim 1, wherein the plane of the connector can be tilted to a distance from the base part, causing the second end to be displaced to a distance that is larger than the height (h) of the retention devices.

11. An infusion set according to claim 1, wherein the retention devices of the infusion part are formed with contact surfaces for engaging with corresponding contact surfaces of the connector retention devices, the contact surfaces having a plane having a projection of the height (h) perpendicular to the main plane of the base part.

12. An infusion set according to claim 11, wherein the contact surface of the retention devices is essentially perpendicular to the base part.

13. An infusion set according to claim 1, wherein the first fastening means is a mounting pad.

14. An infusion set according to claim 13, wherein the mounting pad is an adhesive dressing.

15. An infusion set according to claim 1, wherein the guide means for positioning the infusion part and the connector relative to each other comprises a tongue and groove connection.

16. An infusion set according to claim 15, wherein the groove is positioned on the head part of the infusion part and the tongue is positioned on the connector part.

17. An infusion set according to claim 1, wherein the head part of the infusion part comprises a transparent portion.

18. An infusion set according to claim 17, wherein the transparent portion of the head part comprises a reduced-thickness.

19. An infusion set according to claim 17, wherein the transparent portion of the head part comprises a magnifying area.

20. A kit comprising an injector device and an infusion set according to claim 1, the injector device comprising:
   a housing
   a plunger slidably received within the housing for movement between an advanced position and a retracted position, the plunger having substantially non-detachably secured thereto an insertion needle for receiving and supporting the cannula of the subcutaneous infusion set in a position with the cannula, where the insertion needle is removable from the cannula while maintaining a transcutaneous placement of the cannula,
   a drive for urging the plunger from the retracted position toward the advanced position to transcutaneously place said cannula of the infusion set received on the insertion needle.

* * * * *